United States Patent [19]

Kerlinger et al.

[11] Patent Number: 4,956,468

[45] Date of Patent: Sep. 11, 1990

[54] PROCESS FOR THE ACYLATION OF THIAZOLIDINES

[75] Inventors: Nancy Kerlinger, Lafayette; Richard D. Gless, Oakland, both of Calif.

[73] Assignee: ICI Americas Inc., Wilmington, Del.

[21] Appl. No.: 405,114

[22] Filed: Sep. 8, 1989

Related U.S. Application Data

[63] Continuation of Ser. No. 270,913, Nov. 14, 1988, abandoned.

[51] Int. Cl.$^5$ .............................................. C07D 277/04
[52] U.S. Cl. ..................................................... 548/200
[58] Field of Search .......................................... 548/200

[56] References Cited

U.S. PATENT DOCUMENTS 4,319,031  3/1982  Teach ................................. 548/200
4,775,676  10/1988  Chiesi ................................. 514/365

OTHER PUBLICATIONS

Gordon, The Chemists Companion, p. 71 (1972).

*Primary Examiner*—Robert Gerstl
*Attorney, Agent, or Firm*—Denis A. Polyn

[57] ABSTRACT

Acylated substituted thiazolidines are formed in high yields by reaction of a substituted thiazolidine with an acyl halide in the presence of a buffer compound. The products are further purified by washing with a strong base. The products are useful as herbicides.

9 Claims, No Drawings

PROCESS FOR THE ACYLATION OF THIAZOLIDINES

This is a continuation of co-pending application Ser. No. 07/270,913 filed on Nov. 14, 1988, now abandoned.

BACKGROUND OF THE INVENTION

The present invention is related to the acylation of thiazolidines using acyl halides in the presence of certain bases.

Substituted thiazolidines of the formula

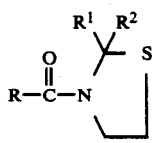

wherein R is haloalkyl, and each of $R^1$ and $R^2$ is hydrogen lower alkyl, are useful as antidotes against crop injury when used with various herbicides. Such compounds are disclosed, for example, in U.S. Pat. No. 4,319,031. Desirous plants such as crop plants can be protected against injury by thiocarbamate-type herbicides, alone or mixed with other herbicides, by adding to the soil a non-phytotoxic antidotally effective amount of a compound of the above formula.

Prior to the present invention, the primary methods for synthesizing these substituted thiazolidines have been by reacting a compound of the above formula (where C(O)—R is replaced by a hydrogen atom) with either (a) an acid halide X—C(O)—R (where X is a halogen) in the presence of NaOH or other caustic (the Schotten-Baumann reaction), or (b) an acid halide X—C(O)—R (where X is a halogen) in the presence of a base such as triethylamine.

Unfortunately, each of these reaction schemes suffers from low yields. In reaction (a) the yield is about 65% or less. In reaction (b) the yield is below 50%.

Additionally, a method for synthesizing other dichloroacetamides by treatment with chloral and sodium cyanide in aqueous sodium carbonate is known (British Patent No. 692,165 (1953); Chem. Abstracts (1954) 48: 8260 g). However, when this method is attempted to produce the above thiazolidines, only a small amount of the desired dichloroacetyl thiazolidine is made, with the major product being diacetyldisulfide.

SUMMARY OF THE INVENTION

The process of the present invention provides acylated substituted thiazolidines in surprisingly increased yields by reaction of the starting material with an acyl halide in the presence of a buffer compound. In a further embodiment of the invention, the product is further purified by washing it with a strong base.

DETAILED DESCRIPTION OF THE INVENTION

More particularly, this invention is directed to a process for the manufacture of a compound having the formula

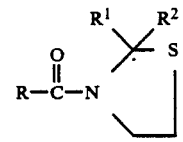

wherein,
R is haloalkyl,
$R^1$ is hydrogen or lower alkyl, and
$R^2$ is hydrogen or lower alkyl;
which process comprises treating a compound having the formula

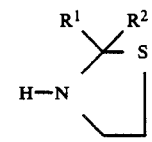

wherein $R^1$ and $R^2$ are as defined above, with an acyl halide of the formula

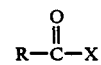

wherein X is a halogen atom and R is as defined above, in the presence of a buffer.

Any material which will function as a buffer, giving resistance to a change in the pH of the reaction mixture and keeping the pH within the desired range, may be used in the present invention. Such buffer substances are normally selected from the salts of weak acids or bases, such as the phosphates, the carbonates, the borates, the acetates and ammonium salts. The buffers useful in the present invention may include, but are not limited to, sodium carbonate, sodium bicarbonate, potassium carbonate, sodium phosphate, sodium orthophosphate, potassium phosphate, calcium hydroxide, borax and the like. Since the preferable pH range for the reaction of the invention is basic, the buffer will preferably be selected from the base buffers.

The buffer is present in the reaction in an amount that serves to keep the reaction within the desired pH range. The quantity used in any particular application will be determined in large part by the individual needs of the manufacturing facility. Factors which enter into such a determination include the cost of the buffer, recovery costs, pH range desired and system capacity. Aside from these considerations, the buffer quantity is not a critical feature of the invention and can vary over a wide range. It will be most convenient to use an amount of buffer which comprises from about 50 to about 250 mole percent, preferably from about 80 to about 200 mole percent based on the starting thiazolidine of formula II.

It has been found that optimum yields are obtained at pH's of 12 or below. When the pH is above about 12 for a significant portion of the reaction, yields decrease with increasing pH. Thus, the preferred range of pH is from about 2 to about 12 more preferably from about 5 to about 11, and most preferably from about 7 to about 10.

The process may successfully be run over a wide range of temperatures. The operating temperature may range from about −10° C. to about 80° C. However, temperature control is often desirable since higher yields of product tend to be obtained at temperatures below about 25° C. The preferable temperature range of the reaction is from about 0° C. to about 15° C. and more preferably from about 2° C. to about 10° C. Temperature control can be achieved by external cooling supplied by any conventional means known in the art, including ice baths, coils, jackets, and the like.

The process does not have a critical operating pressure, but is operable over a wide pressure range, subject only to considerations of economy and materials of construction. It is most convenient, however, to conduct the reaction at approximately atmospheric pressure.

For maximum efficiency, the reaction is preferably run using an excess of the acyl halide. While the amount of excess is purely a question of process economy, such as raw material costs and recovery expenses, the reaction is most conveniently run at an acyl halide excess of up to about 35%.

While the reaction will proceed with no additional water other than that which may be present with the starting thiazolidine of formula II, it is generally preferred to run the reaction in the presence of water for ease of handling and improved reactant contact, with resulting higher yields and use of less starting acyl halide. The amount of water present in the reaction is not critical and can be in the range of from about 0.1 to about 20.0 grams per gram of starting thiazolidine and is preferably from about 1.0 to about 5.0 grams per gram of starting thiazolidine.

A variety of solvents can be used in the practice of the present invention. Any inert solvent can be used, including, but not limited to the following: aliphatic compounds, for example hexane or octane: aromatic compounds, for example benzene, toluene, xylene or mesitylene: chlorinated aliphatic or aromatic compounds, for example methylene chloride, ethylene dichloride or chlorobenzene; ethers, for example 1,2-dimethoxyethane, diethyl ether, tetrahydrofuran or 1,4-dioxane: ketones, for example acetone or methyl isobutyl ketone: and nitriles, for example acetonitrile or butyronitrile.

The acylated thiazolidines produced by the reaction of the invention can be recovered from the reaction mixture by any conventional technique.

In preferred embodiments of the invention, the process further comprises washing the product with a strong base as a purification step. Thus, the acylated thiazolidines may be further treated, following completion of the reaction, with a strong base such as sodium hydroxide, ammonium hydroxide or potassium hydroxide, providing a greatly purified final product.

As used in this specification and the attached claims, the term "haloalkyl" refers to an alkyl group, straight or branched, substituted by one or more halogen atoms. Such halogen is conveniently selected from bromo, chloro and fluoro.

The process of the present invention is particularly useful in synthesizing compounds of formula I where R, $R^1$ and $R^1$ have the following values: R is haloalkyl of 1 to 10 carbon atoms, $R^1$ is hydrogen or lower alkyl of 1 to 4 atoms, and $R^1$ is hydrogen or lower alkyl of 1 to 4 atoms.

Within the scope of the above description, certain embodiments are preferred.

In R, a haloalkyl of 1 to 5 carbon atoms, straight or branched, and substituted with 1 to 3 halogens is preferred. Such halogens are preferably bromo or chloro.

In $R^1$, methyl or ethyl is preferred.

In $R^2$, hydrogen, methyl or ethyl is preferred.

The process of the present invention is further illustrated by the following examples. These examples are offered strictly for purposes of illustration, and are not intended to either limit or to define the invention.

EXAMPLE 1

This example illustrates the preparation of 2,2-dimethyl-N-dichloroacetyl-1,3-thiazolidine according to the invention.

A mixture of sodium carbonate (84.4 g, 0.80 mole). water (204 mL, 11.4 mole) and toluene (1.56 L, 14.7 mole) was cooled in an ice bath to 2° C. and 80 wt % pure aqueous 2.2-dimethyl-1,3-thiazolidine (146.5 g, 1.00 mole, 117.2 g a.i.) was added. Dichloroacetyl chloride (DCAC; 162.1 g, 1.10 mole, Aldrich) was added neat via syringe pump over 65 min. (1.67 mL/min.) to the rapidly stirred reaction mixture, maintaining the internal reaction temperature between 2° and 3° C. During the course of the reaction, gas evolved, additional solids formed and the organic phase turned light yellow. Additional DCAC (12.3 g 0.083 mole) was added at the same rate over 7.4 min. After stirring for 20 min., DCAC (13.7 g. 0.093 mole) was again added at the same rate. After stirring an additional 1 hour, the reaction mixture was warmed to 25° C. by replacing the ice bath with a 35° C. water bath. Upon warming, the previously distinct liquid phases formed an emulsion which dispersed when water (300 mL) was added to dissolve the inorganic solids. The phases were separated, and the toluene solution was washed twice with 80 mL portions of 20% aq. NaOH. The area percent of the side-product N,S-bis(dichloroacetyl)cysteamine was reduced from 10.8% to less than 1% (as measured by HPLC). The toluene solution was then washed with 3N HCl (167 mL). After phase separation, evaporation of the organic layer under reduced pressure for 3 hr gave 210.7 g of 94.0 weight percent pure product (86.8% corrected yield) with a m.p. of 100°–108° C. (compound 1, Table C).

EXAMPLE 2

This example illustrates the preparation of 2,2-dimethyl-N-dichloroacetyl-1,3-thiazolidine using various inorganic bases and solvents and, in comparison, using a strong base, NaOH.

The base to be examined was added to a mixture of 2,2-dimethyl-1,3-thiazolidine (6.0 g, 0.051 mole), 100 mL of solvent and 70 mL of water. A solution of dichloroacetyl chloride (9.8 g, 0.067 mole) diluted to 10 mL with solvent was then added to the vigorously stirred reaction mixture over 67 min., maintaining an internal reaction temperature of ca. 2°–5° C. The reaction mixture was stirred an additional 10 min. after completion of the addition and then filtered if necessary to remove solids. The organic layer was separated, the aqueous layer was washed with methylene chloride (1×40 mL), and the combined organic extracts were dried over $MgSO_4$ and concentrated to afford technical product ("Tech Yield"). Corrected yields ("Corr. Yield") from 2,2-dimethyl-1,3thiazolidine were calculated by weight percent assay of the technical product. 80.3 Weight percent pure aq. 2,2-dimethyl-1,3-thiazolidine was used as starting material except as noted. The results are shown in Table A below.

TABLE A

| Base (Mole %) | DCAC (Mole %) | Solvent | Temp (°C.) | pH Range | Tech Yield | Wt % | Corr. Yield |
|---|---|---|---|---|---|---|---|
| $Na_2PO_4$ (180) | 130 | Toluene | 2–5 | 4.5–9 | 101.5 | 85.6 | 86.9 |
| $NaHCO_3$ (180) | 130 | Toluene | 2–4 | 7–8.5 | 98.5 | 86.5 | 85.2 |
| $Na_2CO_3$ (180) | 130 | Toluene | 2–5 | 9–12 | 100.9 | 85.7 | 86.5 |
| $Na_3PO_4$ (180) | 130 | Toluene | 2–4 | 11–14 | 91.6 | 86.4 | 79.1 |
| NaOH (180) | 130 | Toluene | 2–5 | 12–14 | 49.7 | 88.9 | 44.2 |
| $K_3PO_4{}^a$ (220) | 131 | $EDC^b$ | 1–3 | 7–12 | 99.7 | 79.2 | 87.0 |
| $Na_3PO_4{}^a$ (165) | 131 | Hexane/Acetone | 2–4 | 10–12 | 90.8 | 78.1 | 78.1 |

[a] using 2,2-dimethyl-1,3-thiazolidine, 90.8 weight percent pure
[b] EDC = ethylene dichloride

EXAMPLE 3

This example illustrates the preparation of 2,2-dimethyl-N-dichloroacetyl-1,3-thiazolidine using triethylamine as the base. This is a repetition of the prior art method disclosed in U.S. Pat. No. 3,989,503 (Example 3), which reported a yield of 25%.

2 2-Dimethyl-1,3-thiazolidine (7.5 g, 0.064 mole) and triethylamine (9.0 g, 0.089 mole) were dissolved in 50 mL of ethylene dichloride. The resulting solution was cooled in an ice bath to 3° C. and dichloroacetyl chloride (10.3 g, 0.07 mole) diluted to 20 mL with ethylene dichloride was added via syringe pump over 80 min., with magnetic stirring and maintaining an internal temperature of 2°–4° C. After the addition was complete, the reaction was allowed to stir for an additional 15 min. The reaction mixture was washed with water (2–20 mL) and with 5% aq HCl (2–20 mL), dried over $MgSO_4$, and concentrated at 40° C./20 mm Hg to afford a 76% technical yield of a brownish, gummy solid. This material was found to be 52.1% pure by weight percent assay, corresponding to a yield of 39.6%.

EXAMPLE 4

This example is of the reaction as in Example 3 above but carried out under typical prior art Schotten-Baumann conditions using caustic as the base to prepare 2,2-dimethyl-N-dichloroacetyl-1,3-thiazolidine.

2,2-Dimethyl-1,3-thiazolidine (7.5 g, 0.064 mole) and 20% aq. NaOH (16 mL, 0.096 mole) were dissolved in 50 mL of toluene. The resulting solution was cooled in an ice bath to 4° C. and dichloroacetyl chloride (10.3 g, 0.07 mole) was added via syringe pump over 80 min., with magnetic stirring and maintaining an internal temperature of 4°–5° C. After the addition was complete, the reaction was allowed to stir for an additional 15 min. The reaction mixture was washed with water (2×30 mL), dried over $MgSO_4$ and concentrated at 40° C./20 mm Hg to afford a 83.8% technical yield of a tan, gummy solid. This material was found to be 77.7% pure by weight percent assay, corresponding to a yield of 65.1%.

EXAMPLE 5

This example shows the effect of using a buffer compound, potassium carbonate, versus the prior art sodium hydroxide as the base in the preparation of 2,2-dimethyl-N-dichloroacetyl-1,3-thiazolidine. This example also shows the effects of temperature and the amount of base (buffer or NaOH).

Following the procedure of Example 1 (but without the purification step using NaOH), 2,2-dimethyl-1,3-thiazolidine was reacted with dichloroacetyl chloride in the presence of either potassium carbonate or sodium hydroxide in the amounts and under the temperatures indicated in Table B below. Statistical analysis of the results in the Table show that there was a significant increase in yield due to the use of potassium carbonate, and that use of lower reaction temperatures gave somewhat increased yields with either base.

TABLE B

| Base | Temp (°C.) | Mole % Base | Tech Yield | Wt % | Corr. Yield |
|---|---|---|---|---|---|
| $K_2CO_3$ | 5 | 80 | 99.9 | 87.7 | 87.6 |
| NaOH | 4 | 200 | 89.5 | 87.4 | 78.2 |
| $K_2CO_3$ | 25 | 80 | 98.1 | 83.8 | 82.2 |
| NaOH | 26 | 200 | 86.6 | 76.5 | 66.3 |
| $K_2CO_3$ | 5 | 150 | 101.2 | 87.2 | 88.2 |
| NaOH | 5 | 300 | 86.3 | 85.8 | 74.0 |
| $K_2CO_3$ | 25 | 150 | 95.0 | 85.0 | 80.8 |
| NaOH | 26 | 303 | 72.3 | 90.5 | 65.5 |

EXAMPLE 6

Following the procedures of Example 1, the appropriate unsubstituted, 2-monosubstituted or 2,2-disubstituted 1,3-thiazolidine is reacted with the appropriate haloacyl chloride to give the corresponding haloacylated 1,3-thiazolidines under Table C.

TABLE C $$R-\overset{O}{\underset{\|}{C}}-N\underset{}{\overset{R^1\ R^2}{\diagup\!\!\diagdown\!S}}$$

| Cpd | R | $R^1$ | $R^2$ |
|---|---|---|---|
| 1 | $Cl_2CH$ | $CH_3$ | $CH_3$ |
| 2 | $Cl_3C$ | $CH_3$ | $CH_3$ |
| 3 | $Br_2CH$ | $CH_3$ | $CH_3$ |
| 4 | $CH_3CHBr$ | $CH_3$ | $CH_3$ |
| 5 | $BrCH_2CH_2$ | $CH_3$ | $CH_3$ |
| 6 | $BrCH_2CHBr$ | $CH_3$ | $CH_3$ |
| 7 | $ClCH_2CH_2CH_2$ | $CH_3$ | $CH_3$ |
| 8 | $CH_3CH(Cl)CH_2$ | $CH_3$ | $CH_3$ |
| 9 | $CH_3CH_2CHBr$ | $CH_3$ | $CH_3$ |
| 10 | $CH_3CH_2CH_2CHBr$ | $CH_3$ | $CH_3$ |
| 11 | $BrCH_2CH_2CH_2CH_2CH_2$ | $CH_3$ | $CH_3$ |
| 12 | $Cl_2CH$ | $CH_3$ | $CH_2CH_3$ |
| 13 | $CH_3CHBr$ | $CH_3$ | $CH_2CH_3$ |
| 14 | $BrCH_2CH_2$ | $CH_3$ | $CH_2CH_3$ |
| 15 | $ClCH_2$ | $CH_3$ | $CH_2CH_3$ |
| 16 | $Cl_2CH$ | $CH_2CH_3$ | $CH_3$ |
| 17 | $Br_2CH$ | $CH_2CH_3$ | $CH_3$ |
| 18 | $BrCH_2CHBr$ | $CH_2CH_3$ | $CH_3$ |
| 19 | $Cl_2CH$ | H | H |
| 20 | $BrCH_2$ | H | H |
| 21 | $CH_3CHBr$ | H | H |
| 22 | $BrCH_2CH_2$ | H | H |
| 23 | $BrCH_2CHBr$ | H | H |
| 24 | $(CH_3)_2CBr$ | H | H |

TABLE C-continued $$R-\underset{\underset{O}{\|}}{C}-N\underset{}{\overset{R^1\quad R^2}{\diagdown\!\!\!\diagup}}S$$

| Cpd | R | R¹ | R² |
| --- | --- | --- | --- |
| 25 | ClCH₂CH₂ | H | H |

Although the present invention has been described in some detail by way of example for purposes of clarity and understanding, it will be apparent that other arrangements and equivalents are possible and may be employed without departing from the spirit and scope of the invention. Therefore, the description and illustrations should not be construed as limiting the scope of the invention, which is delineated by the appended claims.

What is claimed is:

1. A process for the manufacture of a compound having the formula $$R-\underset{\underset{O}{\|}}{C}-N\overset{R^1\quad R^2}{\diagdown\!\!\!\diagup}S \quad (I)$$

wherein
R is haloalkyl,
R¹ is hydrogen or lower alkyl, and
R² is hydrogen or lower alkyl; which process comprises treating a compound having the formula $$H-N\overset{R^1\quad R^2}{\diagdown\!\!\!\diagup}S \quad (II)$$

wherein R¹ and R² are defined above, which an acyl halide of the formula $$R-\underset{\underset{O}{\|}}{C}-X \quad (III)$$

wherein X is a halogen atom and R is as defined above, in the presence of a buffer selected from the group of salts of weak bases and acid, wherein said buffer is present in an amount of from about 50 to about 250 mold percent based on the amount of Compound (II) to maintain a pH of from about 5 to about 12, at a temperature of from about 0° C. to about 15° C.

2. A process according to claim 1 wherein said buffer is selected from salts of weak bases.

3. A process according to claim 2 wherein said salts are carbonates or phosphates.

4. A process according to claim 1 wherein said process takes place at a temperature of from about 2° C. to about 10° C.

5. A process according to claim 1 wherein R is haloalkyl of 1 to 10 carbon atoms, R¹ is hydrogen or lower alkyl of 1 to 4 carbon atoms, and R² is hydrogen or lower alkyl of 1 to 4 carbon atoms.

6. A process according to claim 10 wherein R is haloalkyl of 1 to 5 carbon atoms substituted with 1 to 3 halogens selected from bromo and chloro.

7. A process according to claim 11 wherein R¹ is methyl or ethyl and R² is hydrogen, methyl or ethyl.

8. A process according to claim 7 wherein R is dichloromethyl and each of R¹ and R² is methyl.

9. A process for the manufacture and purification of a compound having the formula $$R-\underset{\underset{O}{\|}}{C}-N\overset{R^1\quad R^2}{\diagdown\!\!\!\diagup}S \quad (I)$$

wherein
R is haloalkyl,
R¹ is hydrogen or lower alkyl, and
R² is hydrogen or lower alkyl; which process comprises
(a) treating a compound having the formula $$H-N\overset{R^1\quad R^2}{\diagdown\!\!\!\diagup}S \quad (II)$$

wherein R¹ and R² are as defined above, which an acyl halide of the formula $$R-\underset{\underset{O}{\|}}{C}-X \quad (III)$$

wherein X is a halogen atom and R is as defined above, in the presence of a buffer selected from the group of salts of weak bases and acids, wherein said buffer is present in an amount of from about 50 to about 250 mole percent based on the amount of Compound (II) to maintain a pH of from about 5 to about 12, at a temperature of from about 0° C. about 15° C.; and
(b) washing the crude product with a strong base selected from the group consisting of sodium hydroxide, ammonium hydroxide and potassium hydroxide.

* * * * *